(12) United States Patent
Zimmerman et al.

(10) Patent No.: US 7,700,110 B2
(45) Date of Patent: Apr. 20, 2010

(54) SKIN FIRMING AND LIFTING COMPOSITIONS AND METHODS OF USE

(75) Inventors: Amy C. Zimmerman, Grand Rapids, MI (US); Deborah A. O'Toole, Ionia, MI (US)

(73) Assignee: Access Business Group International LLC, ADA, MI (US)

( * ) Notice: Subject to any disclaimer, the term of this patent is extended or adjusted under 35 U.S.C. 154(b) by 0 days.

(21) Appl. No.: 11/805,017

(22) Filed: May 22, 2007

(65) Prior Publication Data

US 2008/0292651 A1 Nov. 27, 2008

(51) Int. Cl.
| | |
|---|---|
| *A61K 36/02* | (2006.01) |
| *A61K 36/899* | (2006.01) |
| *A61K 36/752* | (2006.01) |
| *A61K 36/48* | (2006.01) |

(52) U.S. Cl. .................. 424/195.15; 424/750; 424/736; 424/757

(58) Field of Classification Search .................. None
See application file for complete search history.

(56) References Cited

U.S. PATENT DOCUMENTS

| 5,972,999 | A | 10/1999 | Murad |
| 6,589,514 | B2 | 7/2003 | Jensen et al. |
| 2003/0235547 | A1 | 12/2003 | Braun et al. |
| 2006/0134131 | A1* | 6/2006 | Gedouin et al. ........ 424/195.17 |
| 2006/0165636 | A1 | 7/2006 | Hasebe et al. |

FOREIGN PATENT DOCUMENTS

| EP | 1520577 | * | 4/2005 |
| JP | 2003012495 | * | 1/2003 |
| JP | 2004224782 | * | 8/2004 |
| JP | 2006241036 | * | 9/2006 |

OTHER PUBLICATIONS

Chemical Business Newsbase. Focus Report; Smooth Operators. Cambridge. Dec. 5, 2005. pp. 1-2.*
Revilla et al. Comparison of Several Procedures Used for the Extraction of Anthocyanins From Red Grapes. J. Agric. Food Chem. 1998. 46, 4592-4597.*
Philipson. New Drugs From Nature-It Could be Yew. Phytotherapy Research. 13, 208. 1999.*
Patent Cooperation Treaty Search Report for PCT/US 08/06207, Sep. 5, 2008.

* cited by examiner

*Primary Examiner*—Patricia Leith
*Assistant Examiner*—Melenie McCormick
(74) *Attorney, Agent, or Firm*—Brinks Hofer Gilson & Lione; G. Peter Nichols

(57) ABSTRACT

Disclosed is a composition comprising a combination of: *Polygonum fagopyrum* seed extract, *Chlorella vulgaris* extract, palmitoyl wheat protein hydrolysate, algae extract, and tripeptide. The composition may further comprise one or more of the following: *Citrus unshiu* peel extract, *Sphacelaria scoparia* extract, *Bambusa vulgaris* extract, *Pisum sativum* (pea) extract, *Evodia rutaecarpa* fruit extract, and dipalmitoylhydroxy proline. Such compositions are useful in methods for aiding in improving skin firmness, lifting the skin, preventing or decreasing skin sagging, and preventing or decreasing visible signs of aging resulting from internal and external causes such as environmental stresses.

9 Claims, 1 Drawing Sheet

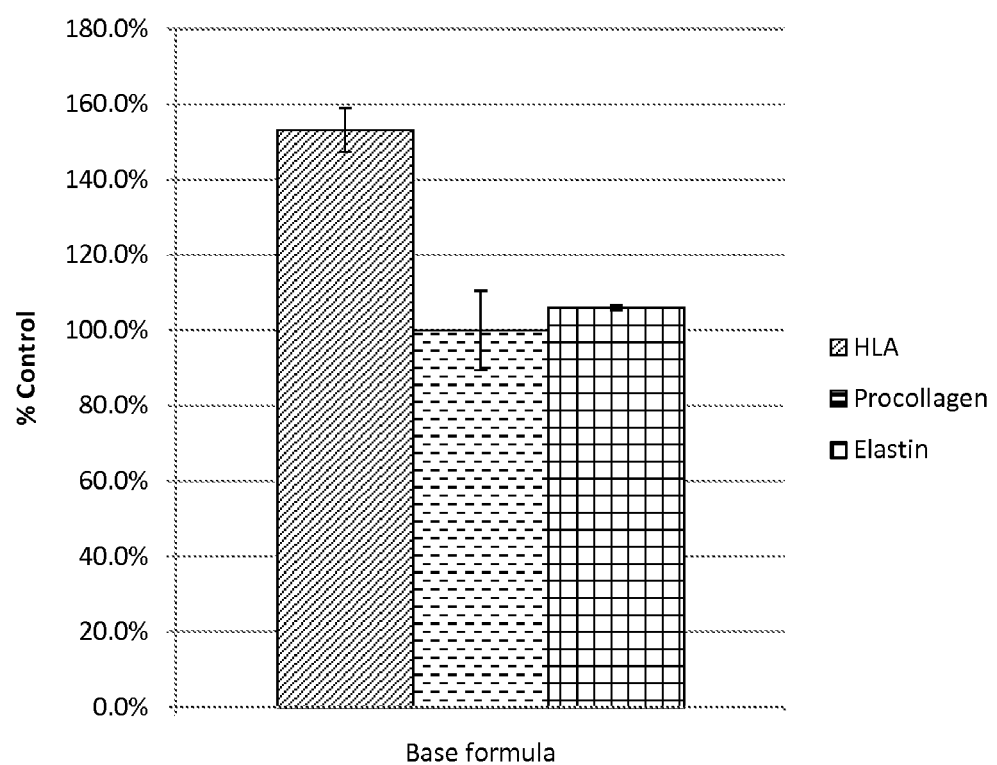

SKIN FIRMING AND LIFTING COMPOSITIONS AND METHODS OF USE

BACKGROUND

A primary goal of cosmetic science is improvement of the outward appearance and health of skin. While the visible signs of aging cannot be fully avoided, they can be dramatically minimized. Less desirable skin traits include wrinkles, fine lines, age spots, uneven skin tone, and loss of firmness or sagging of the skin, which all indicate aged skin. Thus, much of cosmetic science is targeted at treating underlying conditions that cause or stimulate the signs of skin aging.

The underlying conditions causing signs of skin aging can be characterized as intrinsic and extrinsic. Intrinsic causes of skin aging are inevitable and genetically determined; with age, the skin naturally becomes thinner and drier and important skin proteins, including collagen, responsible for maintaining the firmness of skin, and elastin, responsible for maintaining skin's elasticity, are degraded, reduced, and not replaced as quickly as in young skin. Extrinsic causes of skin aging include exposure to sunlight, ultraviolet (UV) light, lifestyle choices such as cigarette smoking, diet, exercise, stress levels, and amount of sleep. Evidence suggests that both intrinsic and extrinsic causes of aging lead to cumulative oxidative damage, which is incurred throughout one's lifetime and ages the skin. For example, UV light generates reactive oxygen species (ROS) in the skin. Oxygen free radicals or ROS are highly reactive species which are known to be a major factor in cell injury via oxidation and subsequent function impairment of lipids, proteins, and nucleic acids. ROS include hydrogen peroxide ($H_2O_2$), the superoxide anion ($O_2^-$), and free radicals such as the hydroxyl radical ($OH^-$). These molecules are unstable and highly reactive, and can damage cells by chemical chain reactions such as lipid peroxidation. Indeed, active oxygen has been suggested as a major cause in not only aging but also several diseases including heart disease and cancer.

Free radicals, ROS, and RNS are known to degrade elastin and collagen in the skin and to decrease the ability of fibroblasts to produce collagen. Collagen is the primary protein of skin. Collagen (in a pre-processed form called pro-collagen) is assembled in cells and consists of three polypeptides wound around each other in a triple helix form, which is stabilized by intrachain disulfide bonds. After the helical molecule is assembled and modified in the cell it is secreted into the extracellular medium and further processed to a mature form (tropocollagen). Matured collagen molecules assemble into fibrils in the extracellular space in a staggered, parallel, fashion wherein the molecules are stabilized in this fibril pattern by covalent cross-linking bonds between the N-terminus of one molecule and the C-terminus of another. The collagen fibrils are interlaced and branched in skin. These interlaced, branched collagen fibrils provide the skin with its shape and firmness. Thus, when collagen is degraded or lost, skin looses its firmness and becomes lax. Another skin protein, elastin, coils and recoils like a spring and accounts for the elasticity of skin. Elastin is normally not produced by the human body after puberty and aging begin. Therefore, to reduce the visible signs of skin aging, such as loss of resiliency, which causes sagging of the skin, it is important to prevent degradation or loss of elastin and/or to stimulate production of elastin.

Like loss of collagen and elastin due to oxidative damage from free radicals, ROS, and RNS, loss of moisture and increased inflammatory responses contribute to skin aging. Indeed, the skin's capacity to inhibit inflammatory responses and retain water decreases with age, making the skin more vulnerable to dehydration and wrinkling. Lipids and fats in the skin help combat water loss by providing an epidermal barrier. This barrier hinders the growth of bacteria, which can cause skin irritation and sensitivity, which leads to increased inflammation and contributes to aging of skin.

The skin employs a host of protective mechanisms to defend itself against the ravages of the environment, free radicals, ROS, and RNS. One of the most widely studied protective mechanisms is the system of free radical scavengers. Free radical scavengers help to protect the skin by neutralizing dangerous substances, such as ROS and RNS, which are generated by sun exposure and pollution. Therefore, a composition containing free radical scavengers along with compounds that stimulate or increase synthesis or production of important skin proteins, such as collagen and elastin, or compounds that reduce or prevent loss or degradation of such proteins are useful for hydrating the skin, inhibiting inflammation of the skin, and lightening or increasing the evenness of skin tone and thereby for improving the appearance, texture, and moisture of the skin and for maintaining general skin health.

BRIEF SUMMARY

In one aspect, the present invention is a composition comprising a beneficial combination of: *Polygonum fagopyrum* seed extract, *Chlorella vulgaris* extract, palmitoyl wheat protein hydrolysate, algae extract, and tripeptide. Such a composition is useful for aiding in improving the firmness of the skin, lifting the skin, preventing or decreasing skin sagging, and preventing or decreasing visible signs of aging such as fine lines, wrinkles, uneven skin tone and age spots resulting from internal and external causes such as sun exposure and other environmental stresses. In one example, the algae extract may comprise an extract of the brown algae *Sphacelaria scoparia*, an extract of the microalga *Nannochloropsis oculata*, or both. In another example, the tripeptide may comprise dipeptide diaminobutyroyl benzlyamide diacetate, glutathione, or both.

In a further aspect, the present invention is a composition comprising a beneficial combination of: approximately 0.25% to approximately 5% by weight of the total composition *Polygonum fagopyrum* extract; approximately 0.05% to approximately 50% by weight of the total composition *Chlorella vulgaris* extract; approximately 0.05% to approximately 10% by weight of the total composition palmitoyl wheat protein hydrolysate; approximately 0.5% to approximately 10% by weight of the total composition algae extract; and approximately 0.05% to approximately 10% by weight of the total composition tripeptide.

In another aspect, the present invention comprises *Polygonum fagopyrum* seed extract, *Chlorella vulgaris* extract, palmitoyl wheat protein hydrolysate, algae extract, tripeptide and one or more of the following: *Citrus unshiu* peel extract, *Sphacelaria scoparia* extract, *Bambusa vulgaris* extract, *Pisum sativum* (pea) extract, *Evodia rutaecarpa* fruit extract, and dipalmitoylhydroxy proline (palmitoyl-1 palmitoyloxy-4 proline).

In a further aspect, the present invention comprises approximately 0.25% to approximately 5% by weight of the total composition *Polygonum fagopyrum* extract; approximately 0.05% to approximately 5% by weight of the total composition *Chlorella vulgaris* extract; approximately 0.05% to approximately 10% by weight of the total composition palmitoyl wheat protein hydrolysate; approximately 0.5% to approximately 10% by weight of the total composition algae extract; approximately 0.05% to approximately 10% by weight of the total composition tripeptide, and if present, comprises approximately 0.05% to approximately 10% by weight of the total composition *Citrus unshiu* peel extract; approximately 0.05% to approximately 5% by weight of the total composition *Sphacelaria scoparia* extract; approximately 0.05% to approximately 10% by weight of the total composition *Bambusa vulgaris* extract; approximately 0.5% to approximately 10% by weight of the total composition *Pisum sativum* extract; approximately 0.05% to 10% by weight of the total composition *Evodia rutaecarpa* fruit extract; and approximately 0.05% to approximately 10% by weight of the total composition dipalmitoylhydroxy proline.

In another aspect, the present invention is a method of improving the firmness of skin comprising administering a composition comprising a beneficial combination of: *Polygonum fagopyrum* seed extract, *Chlorella vulgaris* extract, palmitoyl wheat protein hydrolysate, algae extract, and tripeptide. In one example, the algae extract may comprise an extract of the brown algae *Sphacelaria scoparia*, an extract of the microalga *Nannochloropsis oculata*, or both. In another example, the tripeptide may comprise dipeptide diaminobutyroyl benzlyamide diacetate, glutathione, or both. When used in methods of improving the firmness of skin, the beneficial combination may further comprise one or more of the following: *Citrus unshiu* peel extract, *Sphacelaria scoparia* extract, *Bambusa vulgaris* extract, *Pisum sativum* (pea) extract, *Evodia rutaecarpa* fruit extract, and dipalmitoylhydroxy proline (palmitoyl-1 palmitoyloxy-4 proline).

In a further aspect, the present invention is a method of improving the elasticity or resiliency of skin comprising administering a composition comprising a beneficial combination of: *Polygonum fagopyrum* seed extract, *Chlorella vulgaris* extract, palmitoyl wheat protein hydrolysate, algae extract, and tripeptide. In one example, the algae extract may comprise an extract of the brown algae *Sphacelaria scoparia*, an extract of the microalga *Nannochloropsis oculata*, or both. In another example, the tripeptide may comprise dipeptide diaminobutyroyl benzlyamide diacetate, glutathione, or both. When used in methods of improving the elasticity or resiliency of skin, the beneficial combination may further comprise one or more of the following: *Citrus unshiu* peel extract, *Sphacelaria scoparia* extract, *Bambusa vulgaris* extract, *Pisum sativum* (pea) extract, *Evodia rutaecarpa* fruit extract, and dipalmitoylhydroxy proline (palmitoyl-1 palmitoyloxy-4 proline).

Another aspect of the invention is a method of improving the appearance of skin by reducing or preventing signs of aging such as wrinkles, fine lines, age spots or dark spots, skin discoloration, sagging of the skin, loss of skin firmness and loss of skin elasticity comprising administering a composition comprising a beneficial combination of: *Polygonum fagopyrum* seed extract, *Chlorella vulgaris* extract, palmitoyl wheat protein hydrolysate, algae extract, and tripeptide. In one example, the algae extract may comprise an extract of the brown algae *Sphacelaria scoparia*, an extract of the microalga *Nannochloropsis oculata*, or both. In another example, the tripeptide may comprise dipeptide diaminobutyroyl benzlyamide diacetate, glutathione, or both. When used in such methods, the beneficial combination may further comprise one or more of the following: *Citrus unshiu* peel extract, *Sphacelaria scoparia* extract, *Bambusa vulgaris* extract, *Pisum sativum* (pea) extract, *Evodia rutaecarpa* fruit extract, and dipalmitoylhydroxy proline (palmitoyl-1 palmitoyloxy-4 proline).

BRIEF DESCRIPTION OF THE DRAWINGS

FIG. 1 is a graph illustrating the results of the extracellular matrix synthesis assay described in Example 1.

DETAILED DESCRIPTION

It is to be understood that this invention is not limited to the particular compositions, methodology, or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular examples only, and is not intended to limit the scope of the present invention, which will be limited only by the claims.

The present invention is a composition comprising a beneficial combination of two or more of the following ingredients: *Polygonum fagopyrum* seed extract, *Citrus unshiu* peel extract, *Sphacelaria scoparia* extract, *Chlorella vulgaris* extract, *Bambusa vulgaris* extract, *Pisum sativum* (pea) extract, *Evodia rutaecarpa* fruit extract, palmitoyl wheat protein hydrolysate, dipalmitoylhydroxy proline (palmitoyl-1 palmitoyloxy-4 proline), algae extract, and tripeptide. More specifically, a composition of the present invention comprises a beneficial combination of: *Polygonum fagopyrum* seed extract, *Chlorella vulgaris* extract, palmitoyl wheat protein hydrolysate, algae extract, tripeptide, and rosemary extract. A composition of the present invention also may comprise one or more of the following: *Citrus unshiu* peel extract, *Sphacelaria scoparia* extract, *Bambusa vulgaris* extract, *Pisum sativum* (pea) extract, *Evodia rutaecarpa* fruit extract, and dipalmitoylhydroxy proline (palmitoyl-1 palmitoyloxy-4 proline).

Compositions of the present invention are useful for aiding in improving the firmness of the skin, lifting the skin, preventing or decreasing skin sagging, and preventing or decreasing visible signs of aging, such as fine lines, wrinkles, uneven skin tone, and age spots, resulting from internal and external causes such as sun exposure and other environmental stresses. Thus, the compositions of the present invention also are useful in methods of improving the firmness of skin, the elasticity of skin, and the appearance of skin, as well as in methods of reducing or preventing or decreasing signs of aging such as wrinkles, fine lines, age spots or dark spots, skin discoloration, sagging of the skin, loss of skin firmness and loss of skin elasticity.

The present invention functions, at least in part, by targeting and reducing damage caused by free radicals, ROS, and RNS. In particular, compositions of the present invention are designed to lift the skin thereby preventing or decreasing visible signs of aging, such as those caused by sunlight, UV exposure and other environmental stresses. The compositions of the present invention are useful as early stage treatments that not only protect vital skin molecules such as important proteins and enzymes (e.g. collagen and elastin), but that also stimulate natural processes in the skin that increase or stimulate production or synthesis of these molecules. Other functions of the present invention include: promoting or increasing collagen synthesis; preventing or reducing lipogenesis; preventing or reducing adipocytes; improving microcirculation; inhibiting degradative enzymes such as collagenase and elastase; preventing or decreasing one or more of erythema, inflammation, and oxidation; increasing or stimulating skin tightening, firming, or lifting; decreasing or reducing skin sagging; and stimulating or increasing hyaluronic acid (HA) synthesis in the skin.

A composition of the present invention may comprise a buckwheat wax and/or an extract of buckwheat seed. Buckwheat wax may obtained from the grains of *Polygonum fagopyrum* by a supercritical $CO_2$ extraction method. Buckwheat wax is rich in phytosterol, mainly β-sitosterol and campesterol. Buckwheat wax, a pale green wax with a characteristic odor, is useful for inhibiting or reducing lipogenesis. Lipogenesis is the process by which glucose is converted into fatty acids. An extract of buckwheat (or *Polygonum fagopyrum*) seed may be obtained using any extraction method known in the art. In one example, buckwheat wax, or an extract of buckwheat seed may form from approximately 0.25% to approximately 5% by weight of the composition. In a specific example, buckwheat wax or an extract of buckwheat seed may form approximately 1% by weight of a composition of the present invention. Buckwheat wax is commercially available from Barnet Products Corporation (Englewood Cliff, N.J.).

Extracts of the brown algae *Sphacelaria scoparia*, such as SCOPARIANE™, a hydroglycolic extract, also may be included in compositions of the present invention. Extracts of *Sphacelaria scoparia* inhibit adipocyte differentiation by controlling the expression of fatty acid synthase (FAS) and stearoyl-CoA desaturase (SCD-1). Simultaneously, extracts of *Sphacelaria scoparia* help firm the skin by increasing collagen synthesis. SCOPARIANE™, a commercially available extract of *Sphacelaria scoparia* (Barnet, Engelwood Cliffs, N.J.), is a honey-colored water soluble liquid with a characteristic odor. In one example, an extract of *Sphacelaria scoparia*, for example SCOPARIANE™, forms approximately 0.05% to approximately 5% by weight of the composition. In a specific example, an extract of *Sphacelaria scoparia* may form approximately 1-2.5% by weight of the composition.

A composition of the present invention also may comprise an aqueous extract of the green microalga *Chlorella vulgaris*, for example DDERMOCHLORELLA™ D, commercially available from Barnet Products Corporation (Englewood Cliffs, N.J.). Aqueous extracts of *Chlorella vulgaris* are rich in amino acids such as lysine, proline, glycine, and alanine, which are the essential building blocks of proteins. Extracts of *Chlorella vulgaris* stimulate collagen synthesis, inhibit collagenase and inhibit elastase. In one example, an aqueous extract of *Chlorella vulgaris* forms from approximately 0.05% to approximately 5% by weight of the composition. In another example, an aqueous extract of *Chlorella vulgaris* forms from approximately 0.5% to approximately 2% by weight of the composition.

Palmitoyl wheat protein hydrolysate (or palmitoyl hydrolyzed wheat protein) may be included in a composition of the present invention. It is commercially available from Seppic (subsidiary of Air Liquide, France) as Deepaline PVB. Palmitoyl wheat protein hydrolysate is a wheat bioprotein that has a rapid relaxing mechanical action to smooth out facial expression wrinkles and a long term redensifying biological action on dermal and epidermal cells and thereby lastingly fills deep lines and wrinkles. In one example, palmitoyl wheat protein hydrolysate may form from approximately 0.05% to approximately 10% by weight of the total composition. In other examples, palmitoyl wheat protein hydrolysate may form from approximately 0.1% to approximately 5% by weight of the total composition; or from approximately 0.25% to approximately 2% by weight of the composition.

A composition of the present invention also may comprise a tripeptide, for example, glutathione (2-amino-5-{[2-[(carboxymethyl)amino]-1-(mercaptomethyl)-2-oxoethyl] amino}-5-oxopentanoic acid or γ-glutamylcysteinylglycine). Tripeptide refers to a peptide consisting of three amino acids joined by peptide bonds. In one example, a tripeptide may form from approximately 0.05% to approximately 10% by weight of the total composition. In other examples, a tripeptide may form from approximately 0.25% to approximately 5% by weight of the total composition; or from approximately 0.5% to approximately 2% by weight of the composition.

In addition to glutathione, some examples of tripeptides that may be included in the present invention are: thyrotropin-releasing hormone (TRH, thyroliberin or protirelin) (L-pyroglutamyl-L-histidinyl-L-prolinamide), which is a peptide hormone that stimulates the release of thyroid-stimulating hormone and prolactin by the anterior pituitary; melanostatin (prolyl-leucyl-glycinamide), which is a peptide hormone produced in the hypothalamus that inhibits the release of melanocyte-stimulating hormone (MSH); ophthalmic acid (L-γ-glutamyl-L-α-aminobutyryl-glycine) or norophthalmic acid (γ-glutamyl-alanyl-glycine), which are analogues of glutathione isolated from crystalline lens; and eisenin (pGlu-Gln-Ala-OH), which is a peptide with immunological activity isolated from the Japanese marine alga *Elsenia bicylis*. Some tripeptides are commercially available. For example, Tripeptide-1, known as LIPOREDUCTYL®, is a proprietary, specialized molecule that is a synthetic peptide containing three amino acid residues-glycerine, histidine, and lysine, which is commercially available from Lipotech in Barcelona, Spain.

SYN®-AKE (dipeptide diaminobutyroyl benzylamide diacetate), commercially available from Centerchem, Inc. (Norwalk, Conn.), is another example of a tripeptide that may be used in the present invention. SYN®-AKE functions in a manner similar to Waglerin 1, a neuromuscular blocking compound found in the venom of the Temple Viper. Specifically, SYN®-AKE acts at the post-synaptic membrane as a reversible antagonist of the muscular nicotinic acetylcholine receptor (mnAchR) by preventing binding of acetylcholine to the receptor, causing the receptor to remain closed and the muscles to stay relaxed. In one example, SYN®-AKE may form from approximately 0.1% to approximately 10% by weight of the composition. In a further example, SYN®-AKE may form from approximately 0.25% to approximately 8% by weight of the total composition or from approximately 0.5% to approximately 5% by weight of the total composition.

A composition of the present invention may comprise an extract of the microalga *Nannochloropsis oculata*. One commercially available example of such an extract is PEPHA®-TIGHT, available from Centerchem, Inc. (Norwalk, Conn.). Extracts of *Nannochloropsis oculata* function to firm skin by providing a thin film covering the skin and exerting an instant perceptible tightening effect and a longer term effect based on stimulation of collagen-1. In one example, an extract of *Nannochloropsis oculata* forms from approximately 0.5% to approximately 10% by weight of the total composition. In another example, an extract of *Nannochloropsis oculata* forms from approximately 1% to approximately 8% by weight of the total composition, or from approximately 2% to approximately 5% by weight of the total composition.

An extract of *Evodia rutaecarpa* fruit also may be included in a composition of the present invention. One example of a commercially available extract of *Evodia rutaecarpa* fruit is Evodiox, available from Barnet Products Corporation (Englewood Cliffs, N.J.). Another example of an extract of *Evodia rutaecarpa* is the ancient elixir Wu-Zhu-Yu (or Wu-Chu-Yu), which has been used for generations in China to soothe inflammation, reduce pain, relieve indigestion and ulcers, and heal wounds. Extracts of *Evodia rutaecarpa* have been shown to inhibit release of prostaglandin-E2 (PGE-2), reduce erythema, and reduce inflammation. In one example, an extract of *Evodia rutaecarpa* fruit may form from approximately 0.05% to approximately 10% by weight of the composition. In other examples, an extract of *Evodia rutaecarpa* fruit may form from approximately 0.1% to approximately 5% by weight of the composition; or from approximately 0.1% to approximately 2% by weight of the composition.

A composition of the present invention also may comprise an extract of *Citrus unshiu* peel. *Citrus unshiu* also is referred to as the Satsuma mandarin or the Satsuma tangerine. In one example, an extract of *Citrus unshiu* may form from approximately 0.05% to approximately 10% by weight of the composition. In other examples, an extract of *Citrus unshiu* may form from approximately 0.1% to approximately 5% by weight of the composition; or from approximately 0.1% to approximately 2% by weight of the composition.

Dipalmitoylhydroxy proline (or palmitoyl-1 palmitoyloxy-4 proline) also may be included in a composition of the present invention. Dipalmitoylhydroxy Proline, commercially available as SEPALIFT® DPHP from Seppic (subsidiary of Air Liquide, France), is a plant-derived material that smoothes over existing wrinkles and prevents the development of new ones by stimulating the contraction of collagen fibers and by preventing enzyme destruction of dermal fibers. It also moisturizes and rejuvenates facial skin as well as restores firmness of skin. In one example, dipalmitoylhydroxy proline may form from approximately 0.05% to approximately 10% by weight of the composition. In other examples, dipalmitoylhydroxy proline may form from approximately 0.1% to approximately 5% by weight of the composition; or from approximately 0.1% to approximately 2% by weight of the composition.

Extracts of bamboo, for example a *Bambusa vulgaris* extract, may be included in compositions of the present invention. Bamboo extracts are effective free radical scavengers, and are known to help enhance collagen synthesis and stimulate production of hyaluronic acid. In one example, an extract of bamboo may form from approximately 0.05% to approximately 10% by weight of the composition. In other examples, an extract of bamboo may form from approximately 0.25% to approximately 5% by weight of the composition; or from approximately 0.5% to approximately 2% by weight of the composition.

A composition of the present invention also may include an extract of *Pisum sativum*, or a pea extract. Pea extracts reinforce the skin's natural defenses and help fight against free radicals generated by harmful environmental factors. In one example, a pea extract may form from approximately 0.05% to approximately 10% by weight of the composition. In other examples, a pea extract may form from approximately 0.25% to approximately 5% by weight of the composition; or from approximately 0.5% to approximately 2% by weight of the composition.

Rosemary (*Rosmarinus officinalis*) extract may be included in a composition of the present invention. Rosemary extract contains caffeic acid and rosemarinic acid; both are potent antioxidant and anti-inflammatory agents that are useful in preventing and reducing damage caused by free radicals. In one example, a rosemary extract may form from approximately 0.05% to approximately 10% by weight of the composition. In other examples, a rosemary extract may form from approximately 0.25% to approximately 5% by weight of the composition; or from approximately 0.5% to approximately 2% by weight of the composition.

The above-identified ingredients may be commercially obtained or obtained using any extraction process, including extraction with an organic solvent, supercritical fluid extraction, water extraction, etc. Ingredients useful in the present invention are combined to formulate a composition of the present invention that is useful for providing both immediate and long-term improvement in the health and appearance of skin. Specifically, compositions of the present invention provide an immediate firming/tightening sensation to the skin at application, prevent changes in and loss or degradation of collagen and elastin caused by exposure to sunlight, UV rays and environmental stresses, and boost the skin's natural ability to restore firmness and elasticity by boosting collagen, elastin, and glycosaminoglycan (GAG) production and synthesis and/or by reducing loss or degradation of collagen, elastin, and GAG.

As discussed above, in addition to providing an immediate firming/tightening sensation to the skin at application, the present invention also may help prevent changes in collagen and elastin caused by sunlight and ultra-violet light exposure, environmental stresses, and intrinsic aging. Compositions of the present invention may be comprised of one or more of the following: buckwheat wax; *citrus unshiu* peel extract; *Sphacelaria scoparia* extract; *Cholorella vulgaris* extract; *Evodia rutaecarpa* fruit extract; palmitoyl wheat protein hydrolysate; algae extract; dipeptide diaminobutyroyl benzylamide diacetate; dipalmitoyl hydroxylproline; and *Bambusa vulgaris* extract. Buckwheat wax may be included to help prevent lipogenesis. *Citrus unshiu* peel extract may be included to help prevent lipogenesis, help improve microcirculation, and as an anti-inflammatory ingredient. *Sphacelaria scoparia* extract may be included to help increase collagen synthesis, help prevent lipogenesis, and help prevent adipose tissue formation. *Cholorella vulgaris* extract may be included to help reduce collagenase and elastase formation, and to provide a tightening effect. *Evodia rutaecarpa* fruit extract may be included to help erythema and inflammation. Palmitoyl wheat protein hydrolysate may be included to help enhance collagen synthesis, and provide a tightening effect. Algae extract may be included to help enhance collagen synthesis and provide a tightening effect. Dipeptide diaminobutyroyl benzlyamide diacetate may be included to provide a tightening effect. Dipaimitoyl hydroxy proline may be included to help enhance collagen synthesis, help inhibit collagenase and elastase, and help prevent oxidation. *Bambusa vulgaris* extract may be included to help enhance collagen synthesis, and to help stimulate production of hyaluronic acid.

A composition of the present invention may achieve an immediate skin tightening by using a combination of skin firming ingredients and film forming ingredients. In one example, the skin firming ingredients may be one or more of palmitoyl wheat protein hydrolysate, algae extract, and dipeptide diaminobutyroyl benzlyamide diacetate. In one example, the film forming ingredients may be one or more of polyvinyl pyrilidone, hydroxy propyl chitosan, and panthenol. The latter two ingredients are described in U.S. Pat. No. 6,391,133.

FORMULATIONS OF THE PRESENT INVENTION

One of ordinary skill in the art will appreciate that the above-identified percentages for each of the ingredients of composition of the present invention may be varied in different formulations of the present invention, yet still be within the scope of the present invention. For example, compositions of the present invention may be formulated for leave-on topical administration or for wash or wipe off topical administration. One of ordinary skill in the art will appreciate that a formulation that is to be left-on after application will have a higher concentration (percentage) of ingredients than a formulation that is to be washed or wiped off.

While the ingredients included in compositions of the present invention are useful for improving the appearance of skin by lifting the skin, reducing sagging of the skin, improving firmness of the skin, reducing the appearance of wrinkling and fine lines on the skin, and maintaining an even skin tone, these ingredients are highly active and reactive compounds, which makes their formulation difficult. In addition, many ingredients in compositions of the present invention have characteristic odors that must be overcome to formulate a cosmetically suitable composition of the present invention.

These difficulties are overcome, at least in part, by formulating a composition of the present invention using one or more of the following: hydrogenated lecithin, sodium methyl stearoyl taurate, glycerin, squalane, and hydroxypropylmethyl cellulose stearoxy ether. A composition of the present invention also may be formulated using polydimethylsiloxane, a dimethicone, or a polydiethylsiloxane. Polydiethysiloxanes offer the same beneficial properties as dimethicones but have improved compatibility with commonly used cosmetic waxes and oils. Specifically, low surface tensions enable polydiethylsiloxanes to spread easily on skin and hair, acting as a lubricant and de-tackifying agent. Polydiethylsiloxanes have a slippery, emollient, yet non-greasy skin feel with more body and cushion than dimethicones of equal viscosities. Further, unlike dimethicone, polydiethylsiloxanes wet pigments well, which is a useful property when formulating color cosmetics. Films of polydiethylsiloxane are hydrophobic but non-occlusive, being permeable to gases, including moisture vapor, similar to dimethyl fluids.

Compositions of the present invention also may be formulated using a variety of different humectants, including but not limited to: dibutyl phthalate; soluble collagen; sorbitol; or sodium 2-pyrrolidone-5-carboxylate. Other examples of humectants that may be used in formulating compositions of the present invention can be found in the CTFA Cosmetic Ingredient Handbook, the relevant portions of which are incorporated herein by reference.

Further, compositions of the present invention may be formulated using one or more emollients including but not limited to: butane-1,3-diol; cetyl palmitate; dimethylpolysiloxane; glyceryl monoricinoleate; glyceryl monostearate; isobutyl palmitate; isocetyl stearate; isopropyl palmitate; isopropyl stearate; butyl stearate; isopropyl laurate; hexyl laurate; decyl oleate; isopropyl myristate; lauryl lactate; octadecan-2-ol; caprylic triglyceride; capric triglyceride; polyethylene glycol; propane-1,2-diol; triethylene glycol; sesame oil; coconut oil; safflower oil; isoamyl laurate; nonoxynol-9; panthenol; hydrogenated vegetable oil; tocopheryl acetate; tocopheryl linoleate; allantoin; propylene glycol; arachis oil; castor oil; isostearic acid; palmitic acid; isopropyl linoleate; lauryl lactate; myristyl lactate; decyl oleate; or myristyl myristate. Other examples of emollients that may be used in formulating composition of the present invention can be found in the CTFA Cosmetic Ingredient Handbook, the relevant portions of which are incorporated herein by reference.

In further examples, formulations of the present invention may additionally comprise one or more penetration enhancers including but not limited to: pyrrolidones, for example 2-pyrrolidone; alcohols, such as ethanol; alkanols, such as decanol; glycols, such as propylene glycol, dipropylene glycol, butylenes glycol; or terpenes.

The formulations of the present invention may also contain various known and conventional cosmetic adjuvants so long as they do not detrimentally affect the desired function of the compositions of the present invention. For example, a composition of the present invention can further include one or more additives or other optional ingredients well known in the art, which can include but are not limited to fillers (e.g., solid, semi-solid, liquid, etc.); carriers; diluents; thickening agents; gelling agents; vitamins, retinoids, and retinols (e.g., vitamin $B_3$, vitamin A, etc.); pigments; fragrances; sunscreens and sunblocks; exfoliants; skin conditioners; moisturizers; ceramides, pseudoceramides, phospholipids, sphingolipids, cholesterol, glucosamine, pharmaceutically acceptable penetrating agents (e.g., n-decylmethyl sulfoxide, lecithin organogels, tyrosine, lysine, etc.); preservatives; antimicrobial agents; amino acids such as proline, pyrrolidone carboxylic acid, its derivatives and salts, saccharide isomerate, buffers together with a base such as triethanolamine or sodium hydroxide; waxes, such as beeswax, ozokerite wax, paraffin wax; plant extracts, such as Aloe Vera, cornflower, witch hazel, elderflower, or cucumber and combinations thereof. Other suitable additives and/or adjuncts are described in U.S. Pat. No. 6,184,247, the entire contents of which are incorporated herein by reference.

The compositions of the present invention also can include additional inactive ingredients, including, but not limited to co-solvents, and excipients. Useful co-solvents include alcohols and polyols, polyethylene glycols ethers, amides, esters, other suitable co-solvents, and mixtures thereof. The compositions of the present invention can also include excipients or additives such as sweeteners, flavorants, colorants, antioxidants, preservatives, chelating agents, viscomodulators, tonicifiers, odorants, opacifiers, suspending agents, binders, and mixtures thereof.

Other additives that may be included in compositions of the present invention will be apparent to those of skill in the art and are included within the scope of the present invention.

Modes of Administration

The compositions of the present invention may be topically administered, administered by injection or orally administered. Generally, the compositions of the present invention are administered at least on a daily basis. Administration of the compositions of the invention may continue for any suitable period of time. It should be appreciated that the degree of cosmetic enhancement will vary directly with the total amount and frequency of composition used.

Useful dosage forms can be prepared by methods and techniques that will be well understood by those of skill in the art and may include the use of additional ingredients in producing appropriate dosage forms. For example, as discussed above, a formulation of the present invention may be intended as a leave-on formulation or as a wash or wipe-off formulation. In one example, a formulation of the present invention is topically administered at least once a day. In another example, a formulation of the present invention may be administered twice daily. In a further example, the formulation may be administered three to five times daily. In another example, there is no limit on the amount of the formulation that might be administered daily.

It is intended that the foregoing detailed description be regarded as illustrative rather than limiting. The present invention is further illustrated by the following experimental investigations and examples, which should not be construed as limiting. The contents of all references, patents and published applications cited throughout this patent are hereby incorporated by reference herein.

EXAMPLES

Example 1

In Vitro Extracellular Matrix Synthesis Assays

Human Hs27 fibroblasts and HEK001 keratinocytes were purchased from ATCC (Manassas, Va.). Co-cultures were incubated in 24 well plates at a ratio of 1:4 respectively. After the incubation period, the media was replaced and the cells were exposed to a test sample (0.1% or 1% v/v) and incubated overnight. The test sample comprised: DOT-9002-14A; *Citrus unshiu* extract; Algae (Pullan and/or *Nannochioropsis oculata* (e.g. PEPHA®-TIGHT); extract of *Sphacelaria scoparia* (e.g. SCOPARIANE™); extract of *Chlorella vulgaris* (e.g. DERMOCHLORELLA™ D); pea extract; bamboo extract; and tripeptide.

After overnight incubation with the test samples, supernatants were collected from the cell cultures and analyzed for the presence of α-elastin, pro-collagen, and hyaluronic acid. Elastin was assayed using the FASTIN™ Elastin Kit from Biocolor, Inc. (Newtownabbey, Northern Ireland). See Liao J., Vesely I. 2004. "Relationship between collagen fibrils, glycosaminoglycans, and stress relaxation in mitral valve chordae tendineae." *Ann Biomed Eng.* 32:977-983.

The results of this assay are reported in FIG. 1. These results show that the test sample induced hyaluronic acid.

Example 2

Evaluation of the Skin Lifting Benefits

A three week, controlled clinical study was conducted to assess the performance and efficacy of a composition comprising a lifting serum of the present invention. Specifically, the lifting serum formulation tested in this three week study comprised the following (all percentages reported below are by total weight of the composition):

Vehicle: water
Emulsifier: a composition comprising hydrogenated lecithin, sodium methyl stearoyl taurate, glycerin, squalane, hydroxypropylmethyl cellulose stearoxy ether, and vegetable sorbitan stearate
Skin Conditioning agents: caffeine; dipotassium glycyrrhizate; panthenol; ethoxydiglycol; proline; a composition comprising C12-15 alkyl benzoate, dipropylene glycol dibenzoate, PPG-15 stearyl ether benzoate; caprylic/capric triglyceride; di-C12-15 alkylfumarate; cetyl alcohol; a composition comprising polyacrylate 13, polyisobutene, and polysorbate 20; polydiethylsiloxane; cyclopentasiloxane; a composition comprising HDI/Trimethlol hexyllactone crosspolymer and silica; butylene glycol; sodium hyaluronate; a composition comprising water, glycerin, lecithin, ceramide 3, and Beta-sitosterol; and a composition comprising water, *Rosmarinus officinalis* leaf extract, and lecithin
Film forming agents: PVP and hydroxypropyl chitosan
pH Adjustor: arginine
Humectants: glycerin
Preservatives: disodium EDTA, chlorphenesin powder, and methylparaben
Firming/Lifting agents: dipalmitoyl hydroxyproline; palmitoyl hydrolyzed wheat protein; a composition comprising *Polygonum fagopyrum* seed extract, caprylic/capric triglyceride, and hydrogenated vegetable oil; a composition comprising water, algae extract, and pullulan water; a composition comprising water, dipropylene glycol, and *Sphacelaria scoparia* extract; a composition comprising water and *Chlorella vulgaris* extract; a composition comprising *Bambusa vulgaris* extract, *Pisum sativum* extract, and glucosamine HCL; a composition comprising *Evodia rutaecarpa* fruit extract and butylene glycol; a composition comprising water, glycerin, and dipeptide diaminobutyroyl benzlyamide diacetate; a composition comprising *Citrus unshiu* peel extract and glycerin; a first derma complex comprising *Centella asiatica* extract, laminaria digitata extract, a composition comprising water and corn extract; and a second derma complex comprising soybean (*Glycine soya*) protein, hydrolyzed rice protein, and sunflower seed extract.
Fragrance: chamomile toner.

The study involved a total of 36 female subjects having mild to moderate skin firmness/laxity and lifting/sagging on the face. Prior to the start of the study, prospective subjects participated in a three-day washout period. During this time, subjects refrained from applying topical moisturizing products to the face but were allowed to continue using their regular brands of moisturizing cleansers, if applicable. During the study, clinical assessments were made using visual expert grading, pinch recoil measurements, and instrumentation (Cutometer, Ballistometer, trans-epidermal water loss). During the course of the study, subjects applied the test material to the entire face each morning and evening. Subjects also applied the test material in the clinic at each visit. Clinic evaluations (clinical grading and instrumental measurements) were periodically performed.

The following procedures were performed at each visit:
Clinical Grading
Subjects were clinically graded globally on the face for firmness/laxity and lifting/sagging.
Pinch Recoil Measurements
Triplicate pinch recoil measurements were taken at the right temple or crow's foot area to assess skin elasticity and resiliency. A trained clinical grader pinched the skin at the test site between the thumb and middle finger, held the skin in place for approximately two seconds, and then recorded the time (to the nearest hundredth of a second) for the skin to return to its original conformation. A decrease in pinch recoil times indicates an increase in skin elasticity/resiliency.
Cutometer Measurements
Cutometer SEM 575 (Courage and Khazaka) measurements were taken on the center of the left cheek to assess the visco-elastic properties (elasticity, firmness, and resiliency) of the skin. The instrument applied a vacuum to a small area of skin and the elastic response of the skin was measured by an optical technique. A vacuum of 300 mbar was applied and released through an 8-millimeter probe.
Ballistometer Measurements
The hand-held Torsional Ballistometer BLS 780 (Dia-Stron Ltd., UK) was used to assess skin visco-elastic properties and general skin firming on the center of the right cheek. A pendulum was dropped on to the skin and the rebound was measured using the Notebook by Labtech (version 7.0) software program. Indentation, alpha, coefficient of restitution and area were obtained from the Ballistometer bounce profile. Multiple measurements were taken at Baseline in order to generate several appropriate K-values (probe height) for future time point comparisons.

TEWL Measurements

The ServoMed Evaporimeter (EP2) was used to measure trans-epidermal water loss (TEWL) on the center of the left cheek. A hand-held probe placed on the skin sampled relative humidity at two points above the skin surface, allowing the rate of water loss to be calculated from the measured humidity gradient.

After completion of Baseline procedures, subjects were distributed a unit of the test material and provided with the following usage/study instructions:

Dispense 3 pumps onto fingertips (approximately the size of a nickel). Using an upward motion, blend into skin until fully absorbed. Start at the lower jaw and move upward to the forehead covering the full face. Use each morning and evening on the face, after your normal cleansing routine (except on the mornings of study visits).

Subjects following these instructions were periodically evaluated.

Biostatistics and Data Management

Table 2, shown below, illustrates the statistically significant differences found for comparisons to Baseline and within-visit comparisons for the clinical grading and instrumentation measurements. An open arrow (⇧⇩) indicates a statistically significant increase/decrease compared to Baseline (Visit 1/Day 0 Pre-Application) values and a closed arrow (↑↓) indicates a significant increase or decrease compared to pre-application values at that visit.

Results of the clinical grading and instrumentation measurements indicate the following test material benefits:

Clinical Grading and Pinch Recoil: Results for clinical grading of firmness/laxity, lifting/sagging, and pinch recoil show significant improvements at each time point compared to that day's baseline and also for each time point compared to pre-application baseline on Day 1 of the study.

Cutometer Measurements: Extensibility showed consistent improvements with long term usage through the duration of the study. Although data for recoil showed no consistent product benefit, resiliency scores showed improvements at the short term time points of nearly every visit.

Ballistometer Measurements: The Ballistometer parameters for "alpha" and "area" did not show meaningful, consistent changes during the course of the study. Beginning after one week of treatment, the data at the 20-minute time points for coefficient of restitution (CoR) showed short and long term improvements (when compared back to Visit 1 baseline and when compared to each visit's baseline). These results show that the product was producing a firming effect on the skin, which is also supported by the significantly lower indentation scores observed at the final study visit (after three weeks of treatment).

TEWL Measurements: TEWL measurements showed only small and sporadic product benefit during the course of the study.

Overall Conclusions

Trans-epidermal water loss (TEWL) measurements did not show consistent short or long term product effect in increasing the skin's barrier function. Short term product benefit for firming/lifting and resiliency was consistently observed via clinical grading and pinch recoil/Cutometer measurements, respectively, as well as by Ballistometer results (coefficient of restitution) starting after two weeks of treatment. Benefits from longer term (at home) usage were documented for firm-

TABLE 2

SUMMARY OF CLINICAL GRADING AND INSTRUMENTATION RESULTS

| | Visit 1 (Baseline/Day 0) | | | Visit 2 (Day 2) | | | | Visit 3 (Day 7) | | Visit 4 (Day 14) | | Visit 5 (Day 21) | |
|---|---|---|---|---|---|---|---|---|---|---|---|---|---|
| | 20 Minutes | 40 minutes | 60 minutes | Pre-App | 20 Minutes | 40 Minutes | 60 Minutes | Pre-App | 20 Minutes | Pre-App | 20 Minutes | Pre-App | 20 Minutes |
| Clinical Grading | | | | | | | | | | | | | |
| Firmness/Laxity | ⇧ | ⇧ | ⇧ | ⇧ | ⇧ ↑ | ⇧ ↑ | ⇧ ↑ | ⇧ | ⇧ ↑ | ⇧ | ⇧ ↑ | ⇧ | ⇧ ↑ |
| Lifting/Sagging | ⇧ | ⇧ | ⇧ | ⇧ | ⇧ ↑ | ⇧ ↑ | ⇧ ↑ | ⇧ | ⇧ ↑ | ⇧ | ⇧ ↑ | ⇧ | ⇧ ↑ |
| Pinch Recoil | ⇩ | ⇩ | ⇩ | ⇩ | ⇩ ↓ | ⇩ ↓ | ⇩ ↓ | ⇩ | ⇩ ↓ | ⇩ | ⇩ ↓ | ⇩ | ⇩ ↓ |
| Cutometer | | | | | | | | | | | | | |
| Extensibility | | | | ⇧ | ⇧ | ⇧ | ↑ | ⇧ | ⇧ ↑ | ⇧ | ⇧ ↓ | ⇧ | ⇧ |
| Recoil at 0.5 | | | | | | | | | ↑ | | | | |
| Recoil at 1.0 | | | | | | | | | ↑ | | | | |
| Resiliency | | ⇧ | | | | | | | ⇧ | | ⇧ | | ⇧ |
| Ballistometer | | | | | | | | | | | | | |
| Alpha | | | | ⇩ | | | | ⇩ | | | | | ⇧ |
| Area | | | | ⇧ | | | | ⇧ | | | | | ⇩ |
| Coefficient of Restitution | | | | | | | | | ⇩ | | ↓ | | ⇩ ↓ |
| Indentation | | | | | | | | | | | | ⇩ | |
| TEWL | | | | | ⇩ | ⇩ | ⇩ | | | | ⇩ | | | ing/lifting [clinical grading, Cutometer and Ballistometer (CoR/indentation) scores] and for resiliency (pinch recoil scores).

Example 3

Irritation, Acnegenicity and Comedogenicity of a Skin Firming Product

A six-week clinical usage study was conducted to determine the irritation, acnegenicity, and comedogeniciy potential of a skin firming product. Fifty-four female subjects with self-perceived acne-prone facial skin, combination dry skin, and who regularly use a moisturizer twice daily on the face completed the study.

At the Baseline visit subjects applied an exaggerated amount of the test material to the eye area (approximately 0.5 grams) in the clinic. During the course of the study, subject applied a formula comprising a composition of the present invention to the face and neck twice daily for the duration of the study. Clinic evaluations were conducted at Baseline, Post-Application at the Baseline visit, Week 3 and Week 6. The formulation of the present invention tested in this study is disclosed in Example 2.

Subjects participated in the following procedures at each visit as indicated:
  Acne Counts Baseline, Week 3, Week 6—An expert clinical grader counted the number of papules, pustules, open comedones, closed comedones, and nodules on each subject's forehead, right cheek, left cheek, and chin.
  Objective irritation grading: Baseline, Week 3, Week 6—Objective irritation parameters (erythema and scaling/dryness) were graded on the left and right sides of the face and eye area.

Subjects showed no increases in objective irritation or in acne lesion counts after 3 and 6 weeks of using the test formulation. Significant decreases were observed in erythema and in most acne lesion counts The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The invention claimed is:

1. A composition consisting essentially of:
  *Polygonum fagopyrum* seed extract,
  aqueous *Chlorella vulgaris* extract,
  palmitoyl wheat protein hydrolysate,
  algae extract, wherein the algae extract is selected from the group consisting of: *Nannochioropsis oculata* extract, *Sphacelaria scoparia* hydroglycolic extract, or both and
  a tripeptide wherein the tripeptide is selected from the group consisting of: dipeptide diamincobutyroyl benzamide diacetate and glutathione or both,
  wherein the composition is effective for aiding in improving the firmness of the skin, lifting the skin, decreasing skin sagging, and decreasing visible signs of aging including one or more of wrinkles, and fine lines.

2. The composition of claim 1, wherein the *Polygonum fagopyrum* seed extract is present in an amount ranging from approximately 0.25% to approximately 5% by weight of the total composition; the aqueous *Chlorella vulgaris* extract is present in an amount ranging from approximately 0.05% to approximately 5% by weight of the total composition; the palmitoyl wheat protein hydrolysate is present in an amount ranging from approximately 0.05% to approximately 10% by weight of the total composition; the algae extract is present in an amount ranging from approximately 0.5% to approximately 10% by weight of the total composition; and the tripeptide is present in an amount ranging from approximately 0.05% to approximately 10% by weight of the total composition.

3. A composition consisting essentially of:
  *Polygonum fagopyrum* seed extract,
  aqueous *Chlorella vulgaris* extract,
  palmitoyl wheat protein hydrolysate,
  algae extract, wherein the algae extract is selected from the group consisting of: aqueous *Chlorella vulgaris* extract, *Nannochloropsis oculata* extract, *Sphacelaria scoparia* hydroglycolic extract, or both,
  a tripeptide wherein the tripeptide is selected from the group consisting of: dipeptide diamincobutyroyl benzamide diacetate and glutathione or both, and one or more of: *Citrus unshiu* peel extract, *Bambusa vulgaris* extract; *Pisum sativum* (pea) extract; *Evodia rutaecarpa* fruit extract, and dipalmitoylhydroxy proline (palmitoyl-1 palmitoyloxy-4 proline),
  wherein the composition is effective for aiding in improving the firmness of the skin, lifting the skin, decreasing skin sagging, and decreasing visible signs of aging including one or more of wrinkles and fine lines.

4. The composition of claim 3, wherein if present the *Citrus unshiu* peel extract is present in an amount ranging from approximately 0.05% to approximately 10% by weight of the total composition; the *Bambusa vulgaris* extract is present in an amount ranging from approximately 0.05% to approximately 10% by weight of the total composition; the *Pisum sativum* extract is present in an amount ranging from approximately 0.5% to approximately 10% by weight of the total composition; the *Evodia rutaecarpa* fruit extract is present in an amount ranging from approximately 0.05% to 10% by weight of the total composition; and the dipalmitoylhydroxy proline is present in an amount ranging from approximately 0.05% to approximately 10% by weight of the total composition.

5. A method of improving skin elasticity or resiliency comprising topically administering an effective amount of the composition of claim 1 to the skin of a subject.

6. The method of claim 5, wherein the *Polygonum fagopyrum* seed extract is present in an amount ranging from approximately 0.25% to approximately 5% by weight of the total composition; the *Chlorella vulgaris* extract is present in an amount ranging from approximately 0.05% to approximately 5% by weight of the total composition; the palmitoyl wheat protein hydrolysate is present in an amount ranging from approximately 0.05% to approximately 10% by weight of the total composition; the algae extract is present in an amount ranging from approximately 0.5% to approximately 10% by weight of the total composition; and the tripeptide is present in an amount ranging from approximately 0.05% to approximately 10% by weight of the total composition.

7. The method of claim 5, wherein the method achieves a decrease in a ballistometer measurement after seven days of twice daily administration of the composition.

8. The method of claim 5, wherein the method achieves a decrease in pinch recoil measurements after seven days of twice daily administration of the composition.

9. A method of improving the appearance and texture of skin comprising topically administering an effective amount of the composition of claim 1 to the skin of a subject.

* * * * *

UNITED STATES PATENT AND TRADEMARK OFFICE
CERTIFICATE OF CORRECTION

PATENT NO. : 7,700,110 B2
APPLICATION NO. : 11/805017
DATED : April 20, 2010
INVENTOR(S) : Amy C. Zimmerman et al.

Page 1 of 1

It is certified that error appears in the above-identified patent and that said Letters Patent is hereby corrected as shown below:

In the Claims

In column 15, claim 1, line 51, after "group consisting of:" replace "*Nannochioropsis*" with --*Nannochloropsis*--.

Signed and Sealed this

Twenty-eighth Day of September, 2010

David J. Kappos
*Director of the United States Patent and Trademark Office*